(12) United States Patent
Kuusela

(10) Patent No.: US 7,397,563 B2
(45) Date of Patent: *Jul. 8, 2008

(54) PASS-LINE INSENSITIVE SENSOR

(75) Inventor: Reijo Kuusela, Kuopio (FI)

(73) Assignee: Honeywell International Inc., Morristown, NJ (US)

( * ) Notice: Subject to any disclaimer, the term of this patent is extended or adjusted under 35 U.S.C. 154(b) by 252 days.

This patent is subject to a terminal disclaimer.

(21) Appl. No.: 11/269,504

(22) Filed: Nov. 8, 2005

(65) Prior Publication Data

US 2007/0103688 A1 May 10, 2007

(51) Int. Cl.
*G01N 21/84* (2006.01)
*G01N 21/55* (2006.01)

(52) U.S. Cl. .................. 356/430; 356/431; 356/445

(58) Field of Classification Search .................. None
See application file for complete search history.

(56) References Cited

U.S. PATENT DOCUMENTS

| | | | |
|---|---|---|---|
| 4,812,665 A | 3/1989 | Puumalainen et al. |
| 4,830,504 A | 5/1989 | Frohardt et al. |
| 4,945,253 A | 7/1990 | Frohardt |
| 5,066,865 A | 11/1991 | Wennerberg |
| 5,943,133 A | 8/1999 | Zeylikovich et al. |
| 6,031,620 A | 2/2000 | Typpo |
| 6,404,502 B2 | 6/2002 | Preston et al. |
| 6,588,118 B2 | 7/2003 | Hellstrom |
| 6,687,015 B1 | 2/2004 | Waller et al. |
| 6,762,839 B2 | 7/2004 | Zeylikovich et al. |
| 6,858,436 B2 | 2/2005 | Zenhausern et al. |

FOREIGN PATENT DOCUMENTS

| WO | WO 98/49541 | 11/1998 |
|---|---|---|
| WO | WO 01/20308 A1 * | 3/2001 |

* cited by examiner

*Primary Examiner*—Gregory J. Toatley, Jr.
*Assistant Examiner*—Amanda H Merlino
(74) *Attorney, Agent, or Firm*—Munck Carter, P.C.

(57) ABSTRACT

Devices, systems and methods for detecting surface characteristics of a sample surface are disclosed. The exemplary system may have a conveying device for moving a sample surface and a light source for reflecting a beam of light off the sample surface. A light detector may receive the beam of light reflected from the sample surface. The area of the beam of light may be unequal to an area of a light detection surface of the light detector. A reference analyzer may determine the optical surface based on a comparison of the reflected light received with known reflected light values for known sample surfaces.

20 Claims, 4 Drawing Sheets

(PRIOR ART)

PASS-LINE INSENSITIVE SENSOR

FIELD OF THE INVENTION

The present invention relates generally to detecting surface characteristics of a sample surface, and more particularly to detecting surface characteristics of a moving sample surface.

BACKGROUND OF THE INVENTION

During the paper making process water, refined pulp and other additives are combined to give the finished paper the desired properties. The mix is spread over a mesh screen which forms the paper and lets the water be extracted. The paper then travels through different processes and machines designed to remove the water from the paper. After the paper is dry, the paper is run between drums to give the desired smoothness. This process may be referred to as calendering the paper. The more times paper is calendered the less bulk it has but the smoother the finish of the paper. To create glossy paper, uncoated paper may be coated with a paint-like product and buffed by rollers under very high pressure, to create a shiny appearance. This process may be referred to as super-calendering. Additional varnish layers may be applied to paper during the printing process to provide a gloss surface on the paper. The gloss surface may also protect the paper from the surrounding environment. During the various manufacturing process a continuous roll of paper weaves throughout the machinery of the press. Rolls and presses are used to move the paper between the various manufacturing processes.

To ensure that the paper surface has received the correct amount of gloss, sensors are used to measure the gloss of sample surfaces. Referring to FIG. 1A, sensor 100A may have light source 102A for providing light beam 104A to illuminate sample surface 106A at a pass-line. Light beam 104A is reflected off sample surface 106A. The intensity of the reflected light is measured with light detector 108A. The reflected light is measured by light detecting surface 110A of light detector 108A to determine the light intensity of the reflected light. The gloss level is calculated by determining the ratio of the reflecting light beam intensity to the intensity of the illuminating light beam. The intensities of the reflected light are compared with known values of intensity for various gloss sample surfaces.

Referring to FIG. 1B, as the paper moves along the manufacturing process, sample surface 106B of a web of paper may flutter or wave due to vibration imparted by the rolling devices, applicators, and other machinery used in the manufacturing process. The flutter or wave may cause the sample surface 106B to move to a new sample surface location 112B. The movement of the sample surface 106B may cause errors to the measured gloss values because the optical arrangement of the gloss sensor system may require a very precise geometry in order to operate in a correct manner.

If sample surface 106B moves from the optimal measurement position, some part of the reflected light rays may be lost and the measured signal will be erratic. The current state of the art may provide for precise measurements in a laboratory setting when the sample position can be easily controlled but, as explained above, such control is not easily obtained in a manufacturing environment.

In paper and board manufacturing, non-touching measurement principles are be preferred over sensor techniques that make contact with the paper web. In addition, paper web stabilization techniques such as mechanical sheet stabilizers are also not preferred. For example, the use of mechanical sheet stabilizers can cause unwanted visible markings or scoring on the product surface. Due to such markings, it may be impossible to use sheet stabilizers in certain applications. Also, sheet stabilizers may tend to increase dust and dirt problems by rubbing the moving web. The cross-direction profiles of paper and board webs can have many types of deviations from a straight line. For example, the base cross profile can be warped in many different directions. Because warping or scoring of paper the optimal position of the paper web for on-line gloss measurement is very difficult and sometimes impossible to guarantee.

Accordingly, an efficient and effective device, method, and system is needed for detecting surface characteristics of a sample surface. In addition, the system and method may provide detecting surface characteristics of a moving sample surface.

SUMMARY OF THE INVENTION

It is, therefore, an object of the present invention to provide devices, systems, and methods for detecting surface characteristics of a sample surface where the surface is stable or moving. According to an exemplary embodiment of the present invention, the device may have a conveying device for moving a sample surface. The device may also have a light source for reflecting a beam of light off the sample surface and a light detector for receiving the beam of light reflected from the sample surface. The area of the beam of light may be unequal to an area of a light detection surface of the light detector. A reference analyzer may determine the optical properties of the analyzed surface based on a comparison of the reflected light received with known reflected light values for known sample surfaces.

In an alternate embodiment, the area of the beam of light may be larger than the area of the light detection surface and the reference analyzer comparison may be based on the area of the detection surface. In another embodiment, the area of the beam may be smaller than the area of the light detection surface and the reference analyzer comparison may be based on the area of the beam of light. In yet another embodiment, the reference analyzer may be used to determine the gloss of the sample surface. In another embodiment, a finishing processing device may be used to increase the gloss characteristics of the sample surface. In another embodiment, the sample surface may be the surface of a moving web of paper. In another embodiment, the reference analyzer compares the intensity of reflected light received with known intensity reflected light values of known sample surfaces.

According to an exemplary embodiment of the present invention, the method may involve the following steps. The sample surface by be conveyed along a mechanized process. A beam of light is emitted on the sample surface and reflected off the sample surface. The beam of light detected from the sample surface. The area of the beam of light may be unequal to an area of a light detection surface of the light detector. The optical surface is determined based a comparison of the reflected beam of light received with known reflected light values for known sample surfaces:

BRIEF DESCRIPTION OF THE DRAWINGS

The above and other objectives and advantages of the present invention will be apparent upon consideration of the following detailed description, taken in conjunction with the accompanying drawings, in which like reference numbers refer to like parts throughout, and in which.

DETAILED DESCRIPTION OF THE INVENTION

A sensor is used to measure the gloss of a sample surface by directing a beam of light at the sample surface and electronically comparing the reflectance of the sample surface to that of a standardization surface having a known gloss. According to an exemplary light source embodiment of the present invention, the light beam illuminating the sample surface has a larger area than the light beam accepted and detected by the light detector. The illuminated area of the sample surface is larger than the area which is seen by the light detector. The illuminated area of the sample surface is larger than the measurement area, which is seen by the light detector. This arrangement allows the sample surface to change its position within predefined geometrical limits. The measurement area of the light detector remains in the illuminated area as the sample surface moves. The intensity of reflected light received by the light detector is compared with known values of intensity for various gloss sample surfaces based on the area of the light detector.

According to an exemplary light detector embodiment, a narrow light beam is used to illuminate the sample surface and is reflected onto a light detector. The illuminated area of the sample surface is smaller than the area which is seen by the light detector. The illuminated area of the sample surface is smaller than the measurement area, which is seen by the light detector. This arrangement allows the sample surface to change its position within the geometrical limits. The measurement area of the beam remains within the detection area of the light detector as the sample surface moves. The intensity of reflected light received by the light detector is compared with known values of intensity for various gloss sample surfaces based on the area of the beam of light. The various embodiments described herein may comply with various known standards, for example, the Technical Association of the Pulp and Paper Industry (TAPPI) standards as well as other known industry and government standards.

Figure 1A:
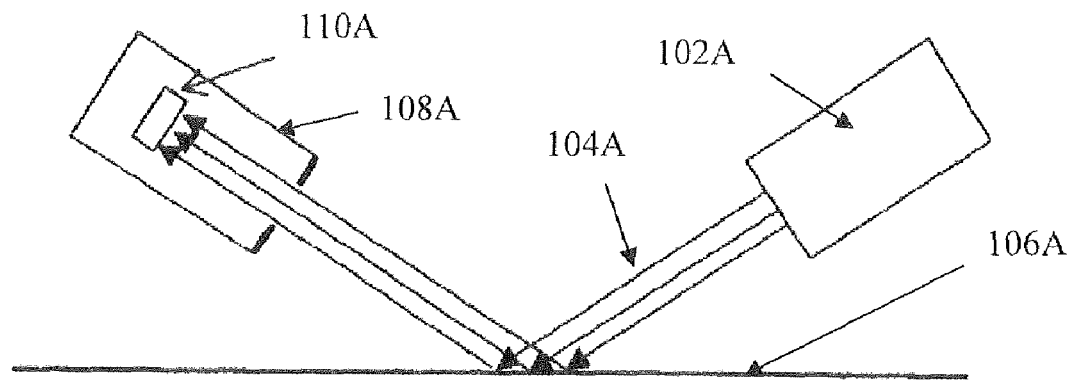
FIG. 1A is a generalized schematic of a prior art gloss sensor.
Figure 1B:
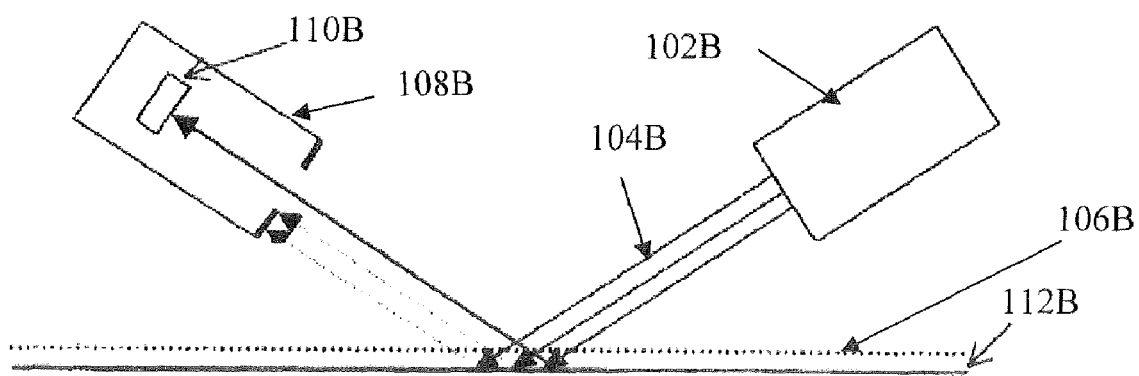
FIG. 1B is a generalized schematic of a prior art gloss sensor with flutters and waves of the sample surface at the pass-line.
Figure 2:
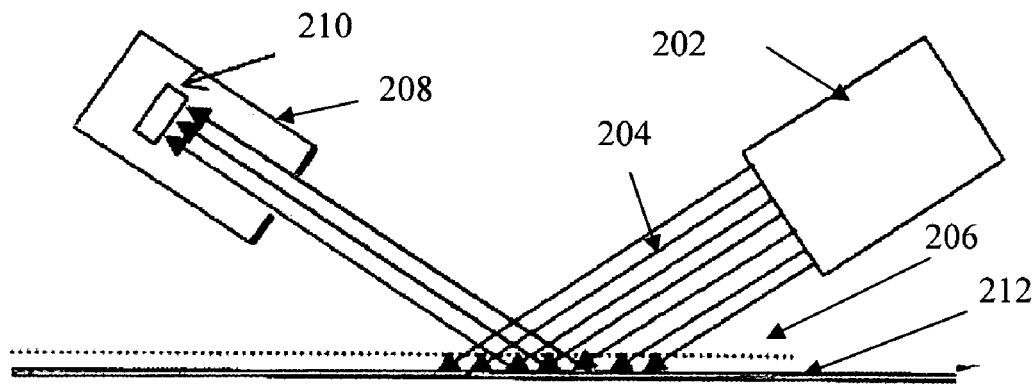
FIG. 2 is a generalized schematic of a sensor used to implement the exemplary light source embodiment of the present invention.

Referring to FIG. 2, sensor 200 may include light source 202 for providing light beam 204 to illuminate sample surface 206 at a pass-line. Light source 202 provides light beam 204 with an area larger than light detection surface 210 of light detector 208. Light source 202 provides a focused beam of light or collimated light beam for example a laser or other method of providing a focused beam of light. Light source 202 may be a variety of electromagnetic energy sources. For example, the light source may emit a non-visible wavelength of light energy to prevent interference by overhead lighting or other sources of light within the manufacturing process.

Sample surface 206 may be a variety of materials handled in a manufacturing process or mechanized process. For example, sample surface 206 may be a web of paper or board. The web is continuously moved throughout the manufacturing process using various rollers, presses, and other machinery. Sample surface 206 is not limited to a web of paper. Sample surface 206 may be individual sheets of material that are advanced on a conveyor belt or devices for transporting sheets of material.

Sensor 200 provides accurate measurements of the sample surface without or with a reduced need for stabilization. Light beam 204 is reflected off the sample surface 206. The intensity of the reflected light is measured with light detector 208. The reflected light is measured by light detecting surface 210 of light detector 208 to determine the light intensity of the reflected beam of light 204. The light detecting surface 210 may define the area seen by the light detector 208.

Light detecting surface 210 converts beam of light 204 into electrical current. Light detecting surface 210 may be composed of a variety of devices, for example, Charge Coupling Devices (CCD), digital Complementary Metal Oxide Semiconductor (CMOS) imaging, or photodiodes, or any other suitable device. The signal generated by light detector 208 may be analog or converted to a digital signal for processing. The signal of light detector 208 is fed into a reference analyzer (not shown).

The reference analyzer compares the intensity of the signal received from light detector 210 with known values of intensity for various gloss sample surfaces. Architecturally in terms of hardware, the reference analyzer may include a processor, memory, and one or more input and output interface devices. The local interface may have additional elements, which are omitted for simplicity, such as controllers, buffers (caches), drivers, repeaters, and receivers, to enable communications. Further, the local interface may include address, control, and/or data connections to enable appropriate communications among the components of a network.

The reference analyzer may determine the gloss level of sample surface 206 by determining the ratio of the reflecting light beam intensity to the intensity of the illuminating light beam from light source 202. The amount of light dispersed by sample surface 206 is used to determine the gloss level of sample surface 206. The reference analyzer may use a stored table, equations, or a combination thereof to compute the gloss level of sample surface 206. As previously stated, gloss level is determined by comparing the ratio of intensity with the intensity of the gloss level for known samples tables of the gloss level.

The systems and methods may also be incorporated in software used with a computer or other suitable operating device of the reference analyzer. The reference analyzer may also include a Graphic User Interface (GUI) to allow the administrator or user to enter, view and store the gloss level or enter constraints associated with the desired gloss level to control other devices of the manufacturing process.

Figure 3:
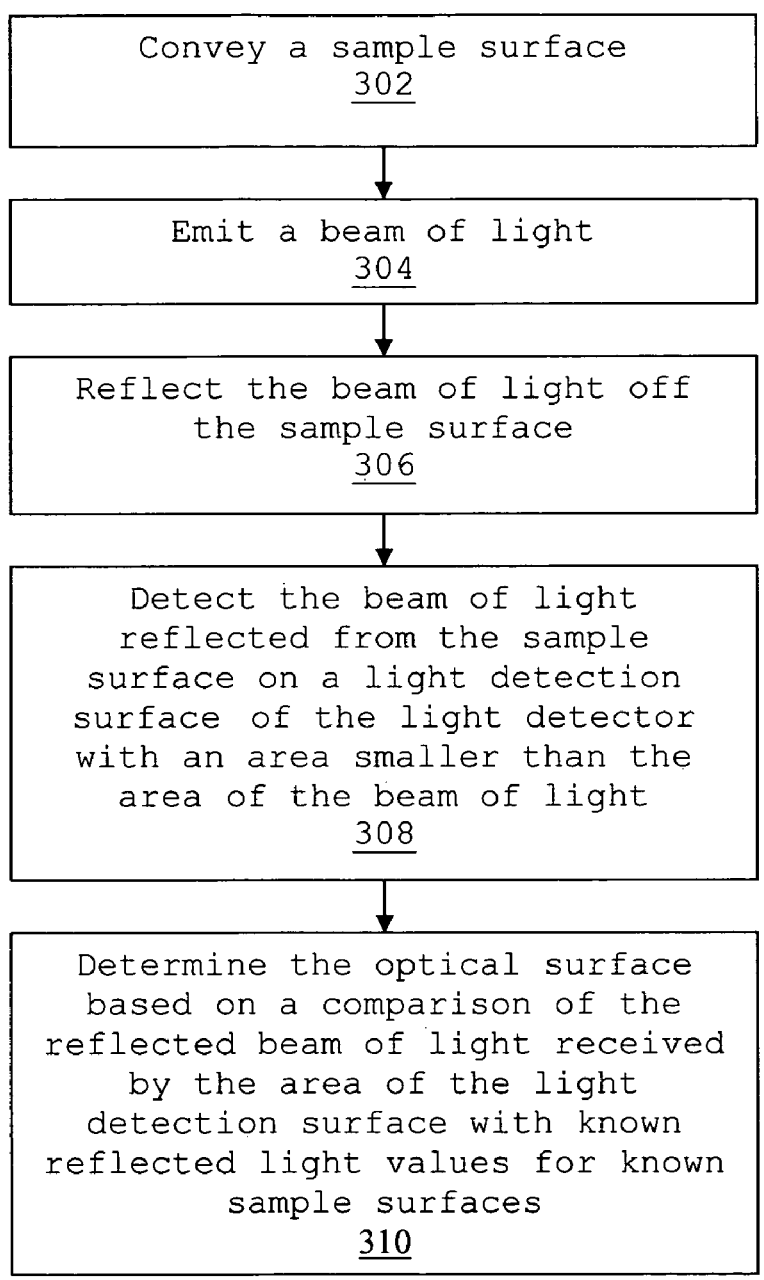
FIG. 3 is a flow chart illustrating an exemplary method for the sensor used to implement the light source embodiment of the present invention.

Referring to FIG. 3, a flow chart illustrates an exemplary method for the sensor used to implement light source embodiment 300 of the present invention. The manufacturing process advances sample surface 206 to the pass-line of sensor 200 (block 302). Light source 202 directs beam of light 204 onto sample surface 206 (block 304). Beam of light 204 is reflected by sample surface 206 (block 306).

The beam of light reflected by the sample surface is detected on light detection surface 210 of light detector 208 (block 308). Light detection surface 210 has an area smaller than the area of beam of light 204. This allows sample surface 206 to flutter or move within a designated geometry. The designated geometry is controlled by the area of beam of light 204 relative to the area of detection on light detecting surface 210. Increasing the area of light beam 204 may increase the amount of movement allowed by sample surface 206 to a new location of sample surface 212. Generally, the area of beam of light 204 is circular; however, the invention may utilize a variety of shapes with either beam of light 204 or the area of light detection surface 210. For example, beam of light 204 may be a circle and the light detection surface 208 may be a square with a width larger than the diameter of beam of light 204. The reference analyzer determines the gloss level of sample surface 206 by comparing the reflected light received from the area of light detection surface 210 with known reflected light values for known sample surfaces based on the area of the light detection surface 210 (block 310).

Figure 4:
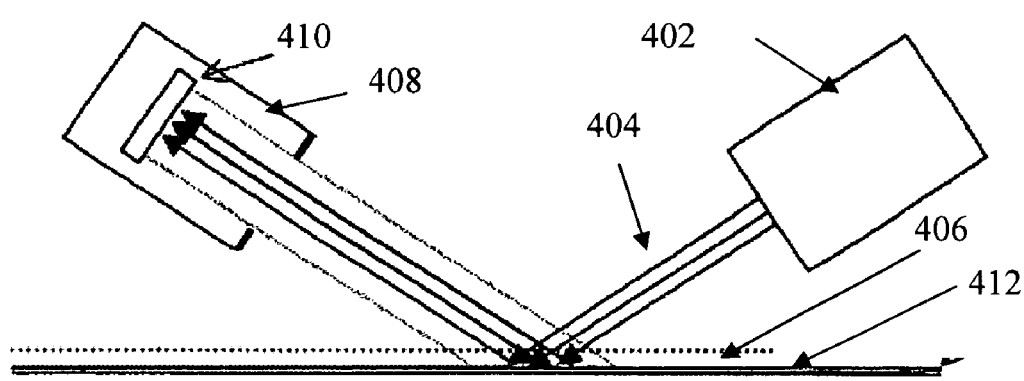
FIG. 4 is a generalized schematic of a sensor used to implement the exemplary light detector embodiment of the present invention.

Referring to FIG. 4, sensor 400 may have a light source 402 for providing light beam 404 to illuminate sample surface 406 at a pass-line. Light source 402 or collimated light beam provides light beam 404 with an area smaller than light detection surface 410 of light detector 408. Light source 402 provides a focused beam of light 404 as previously described with regard to the exemplary light detector embodiment. Sample surface 406 may also be a variety of materials as previously described with regard to the exemplary light source embodiment.

Sensor 400 provides accurate measurements of sample surface 406 without or with a reduced need for stabilization. Light beam 404 is reflected off sample surface 406. The intensity of the reflected light is measured with light detector 408. The reflected light is measured by light detecting surface 410 of light detector 408 to determine the light intensity of the reflected beam of light 404. The light detecting surface 410 may define the area seen by the light detector 408.

Light detecting surface 410 converts beam of light 404 into electrical current using a variety of light detecting elements as previously described with regard to the exemplary light source embodiment. The signal of light detector 408 is fed into a reference analyzer (not shown). The reference analyzer compares the intensity of the signal received from light detector 410 with known values of intensity for various gloss sample surfaces. Architecturally in terms of hardware, the reference analyzer is similar to the reference analyzer of the exemplary light source embodiment as previously described.

The reference analyzer may determine the gloss level of the sample surface 406 by determining the ratio of the reflecting light beam intensity to the intensity of the illuminating light beam from light source 408. The amount of light dispersed by sample surface 406 is used to determine the gloss level of sample surface 406. The reference analyzer may use a stored table or equations to compute the gloss level of the sample surface 406. The gloss level is determined by comparing the ratio of intensity with the intensity of gloss levels for known samples tables of the gloss level.

Figure 5:
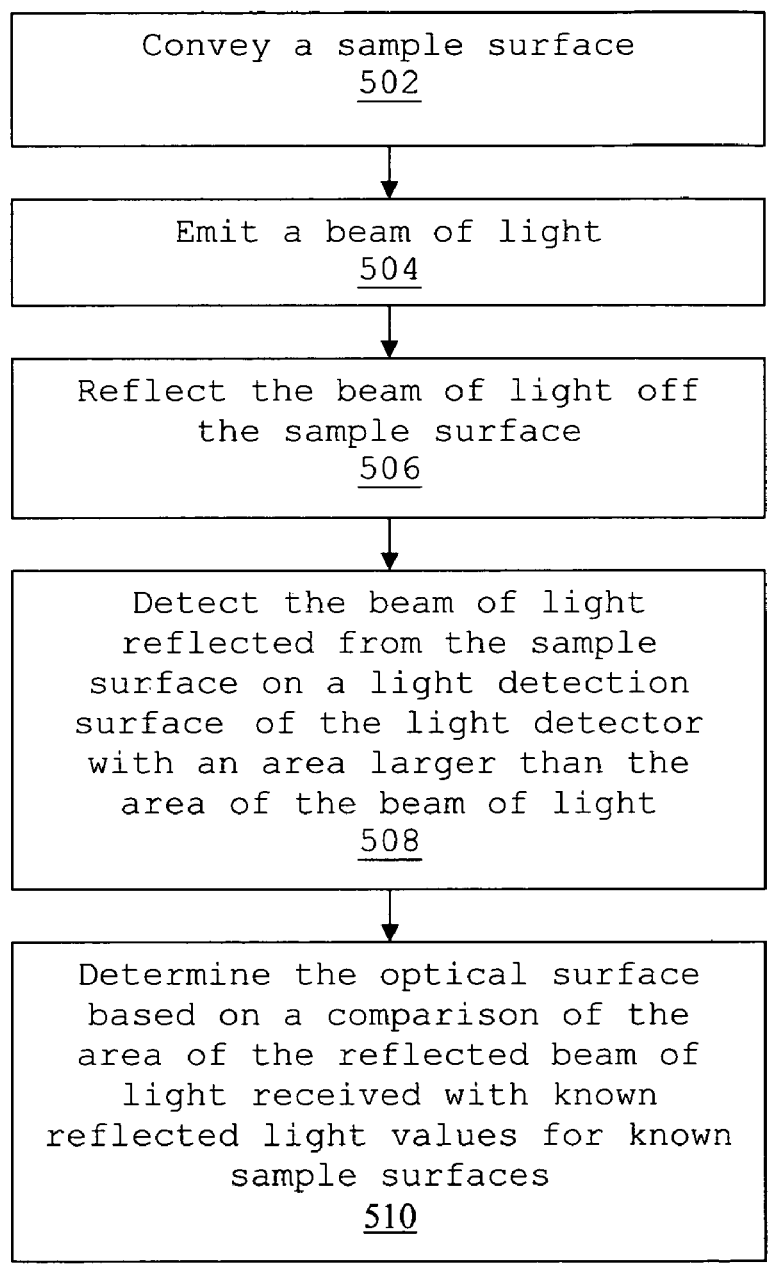
FIG. 5 is a flow chart illustrating an exemplary method for the sensor used to implement the light detector embodiment of the present invention.

Referring to FIG. 5, a flow chart illustrates an exemplary method for the sensor used to implement light detector embodiment 400 of the present invention. The manufacturing process advances sample surface 406 to the pass-line of sensor 400 (block 502). Light source 402 directs beam of light 404 onto sample surface 406 (block 504). Beam of light 404 is reflected by sample surface 406 (block 506).

Beam of light 404 reflected by the sample surface 406 is detected on light detection surface 410 of light detector 408 (block 508). The light detection surface 410 has an area larger than the area of the beam of light 404. This allows sample surface 406 to flutter or move within a designated geometry. The designated geometry is controlled by the area of beam of light 404 relative to the area of detection on light detecting surface 410. Increasing the area of light beam 404 may increase the amount of movement allowed by sample surface 406 to a new location of sample surface 412. The reference analyzer determines the gloss level of the sample surface 406 by comparing the reflected light received from light detection surface 410 with known reflected light values for known sample surfaces based on the area of beam of light 404 (block 510).

It will be understood that the foregoing is only illustrative of the principles of the invention and that various modifications can be made by those skilled in the art without departing from the scope and spirit of the invention. Accordingly, such embodiments will be recognized as within the scope of the present invention. For example, the exemplary embodiments are illustrated as being implemented to determine the gloss level of the sample surface, however, one skilled in the art will appreciate that embodiments of the invention may be implemented with a variety of other surface characteristics.

Persons skilled in the art will also appreciate that the present invention can be practiced by other than the described embodiments, which are presented for purposes of illustration rather than of limitation and that the present invention is limited only by the claims that follow.

What is claimed is:

1. A device comprising:
    a light source for reflecting a beam of light off a sample surface;
    a light detector for receiving the beam of light reflected from the sample surface, wherein an area of the beam of light is unequal to an area of a light detection surface of the light detector when the sample surface is at an optimal measurement position, when the sample surface is closer to the light detector than the optimal measurement position, and when the sample surface is farther from the light detector than the optimal measurement position; and
    a reference analyzer for determining one or more surface characteristics of the sample surface based on a comparison of (i) the reflected light received by the light detector and (ii) known reflected light values for known sample surfaces.

2. The device of claim 1, wherein the area of the beam of light is larger than the area of the light detection surface and the reference analyzer comparison is based on the area of the detection surface.

3. The device of claim 1, wherein the area of the beam of light is smaller than the area of the light detection surface and the reference analyzer comparison is based on the area of the beam of light.

4. The device of claim 1, wherein the reference analyzer determines a gloss of the sample surface.

5. The device of claim 1, further comprising a finish processing device for increasing gloss characteristics of the sample surface.

6. The device of claim 1, wherein the sample surface is a surface of a moving web of paper.

7. The device of claim 1, wherein the reference analyzer compares (i) an intensity of the reflected light received by the light detector and (ii) known intensity reflected light values of the known sample surfaces.

8. A method comprising the acts of:
    emitting a beam of light;
    reflecting the beam of light off a sample surface;
    detecting the beam of light reflected from the sample surfaces, wherein an area of the beam of light is unequal to an area of a light detection surface of a light detector when the sample surface is at an optimal measurement position, when the sample surface is closer to the light detector than the optimal measurement position, and when the sample surface is farther from the light detector than the optimal measurement position; and determining one or more surface characteristics of the sample surface based on a comparison of (i) the reflected beam of light and (ii) known reflected light values for known sample surfaces.

9. The method of claim 8, wherein the area of the beam of light is larger than the area of the light detection surface and the comparison is based on the area of the detection surface.

10. The method of claim 8, wherein the area of the beam is smaller than the area of the light detection surface and the comparison is based on the area of the beam of light.

11. The method of claim 8, wherein determining the one or more surface characteristics of the sample surface involves determining a gloss of the sample surface.

12. The method of claim 8, further comprising:
processing the sample surface to increase a gloss characteristic of the sample surface.

13. The method of claim 8, wherein the sample surface is a surface of a moving web of paper.

14. The method of claim 8, wherein determining the one or more surface characteristics of the sample surface involves comparing (i) an intensity of the reflected light and (ii) known intensity reflected light values of known sample surfaces.

15. A device comprising:
means for reflecting a beam of light off a sample surface of a moving web of material;
means for receiving the beam of light reflected from the sample surface, wherein the diameter of the beam of light is unequal to a diameter of a light detection surface of the receiving means when the sample surface is at an optimal measurement position, when the sample surface is closer to the receiving means than the optimal measurement position, and when the sample surface is farther from the receiving means than the optimal measurement position; and
means for determining one or more surface characteristics of the sample surface based on a comparison of (i) the reflected light received by the receiving means and (ii) known reflected light values for known sample surfaces.

16. The device of claim 15, wherein the diameter of the beam of light is larger than the diameter of the light detection surface and the analyzing means comparison is based on an area of the detection surface.

17. The device of claim 15, wherein the diameter of the beam is smaller than the diameter of the light detection surface and the analyzing means comparison is based on an area of the beam of light.

18. The device of claim 15, wherein the analyzing means determines a gloss of the sample surface.

19. The device of claim 15, wherein the analyzing means compares (i) an intensity of the reflected light received by the receiving means and (ii) known intensity reflected light values of the known sample surfaces.

20. The device of claim 15, wherein the moving web of material is fluttering at a pass-line location of the reflected beam of light.

* * * * *